United States Patent [19]
Seaton et al.

[11] Patent Number: 6,024,480
[45] Date of Patent: Feb. 15, 2000

[54] VIAL PACKAGE FOR A BONE CEMENT MIXER AND DISPENSER

[75] Inventors: James P. Seaton, Chatham, N.J.; Donald Barker, Sandy Hook, Conn.

[73] Assignee: Immedica, Chatham, N.J.

[21] Appl. No.: 09/021,026

[22] Filed: Feb. 9, 1998

[51] Int. Cl.[7] ...................................................... B01F 15/02
[52] U.S. Cl. ...................... 366/130; 366/139; 366/150.1; 366/182.3; 366/189; 206/222; 206/532
[58] Field of Search .................................. 366/139, 150.1, 366/182.3, 182.4, 189, 182.1, 130, 129, 242, 244; 206/219, 222, 532

[56] References Cited

U.S. PATENT DOCUMENTS

| | | |
|---|---|---|
| 4,463,875 | 8/1984 | Tepic . |
| 4,629,347 | 12/1986 | Poppitz . |
| 5,302,358 | 4/1994 | Andersen et al. ...................... 206/532 |
| 5,306,277 | 4/1994 | Bryant et al. . |
| 5,435,645 | 7/1995 | Faccioli et al. ........................... 366/139 |
| 5,588,745 | 12/1996 | Tanaka et al. ........................... 366/139 |

FOREIGN PATENT DOCUMENTS

| | | |
|---|---|---|
| 0380867 A1 | 8/1990 | European Pat. Off. . |
| 0397589 A1 | 11/1990 | European Pat. Off. . |
| 2921565 | 12/1980 | Germany . |
| 3405092 | 8/1984 | Germany ................................. 366/139 |
| 4409610A1 | 9/1995 | Germany . |
| WO93/22041 | 11/1993 | WIPO . |
| WO94/16951 | 8/1994 | WIPO . |
| WO 94/26403 | 11/1994 | WIPO .................................... 366/139 |
| WO94/26403 | 11/1994 | WIPO . |
| WO 94/29012 | 12/1994 | WIPO .................................... 366/139 |
| WO98/20963 | 5/1998 | WIPO . |

*Primary Examiner*—Tony G. Soohoo
*Attorney, Agent, or Firm*—John G. Gilfillan, III; William Squire

[57] ABSTRACT

Lower and upper covers permanently secured together form a vial enclosing chamber in a cap assembly which encloses the top of a bone cement mixing apparatus mixing chamber having prepackaged premeasured bone cement powder. The vial contains a monomer bone cement liquid and may be glass. The vial has two valve seats in corresponding ports on opposing vial side walls sealed by a releaseably secured preferably glass valve member threaded to a nozzle attached to the cap assembly. The vial ports are aligned with a mixing chamber liquid inlet port to permit the cement liquid to flow into the mixing chamber from the opened valves. The vial may be supplied enclosed in a separate package and includes valves on a valve stem attached to the package for opening and sealing the vial. In the alternative, the vial is frangible glass and may be opened by fracturing it and retaining the fragments in the vial receiving chamber to release the liquid to the mixing chamber.

19 Claims, 3 Drawing Sheets

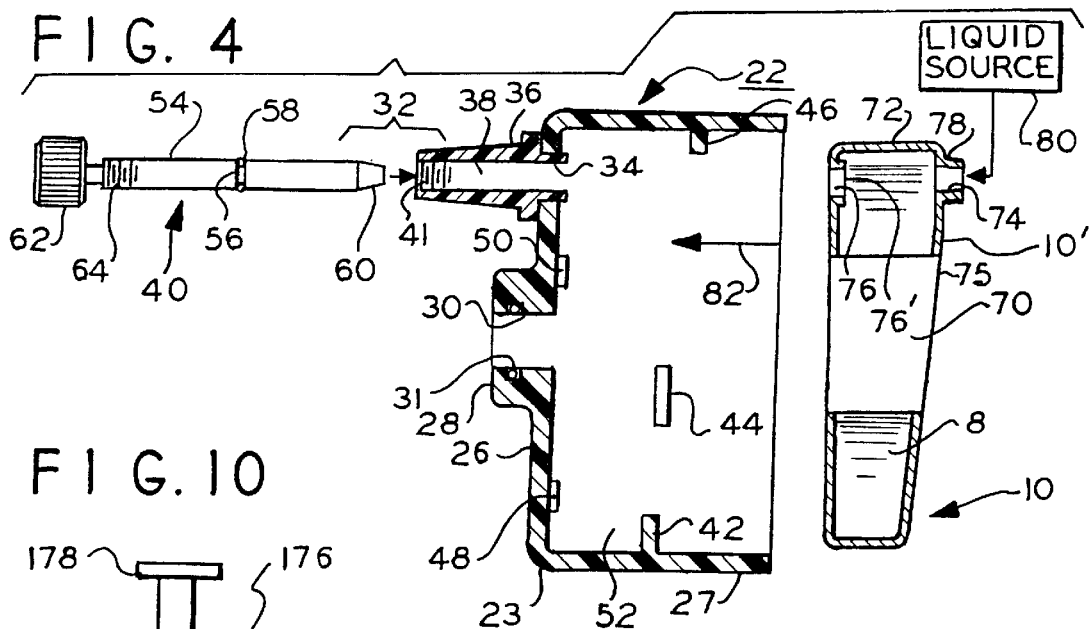
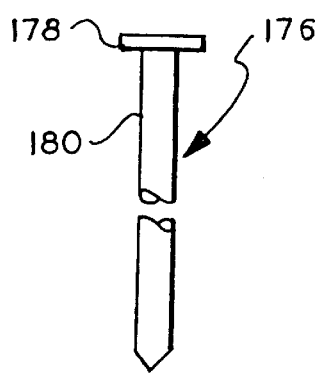
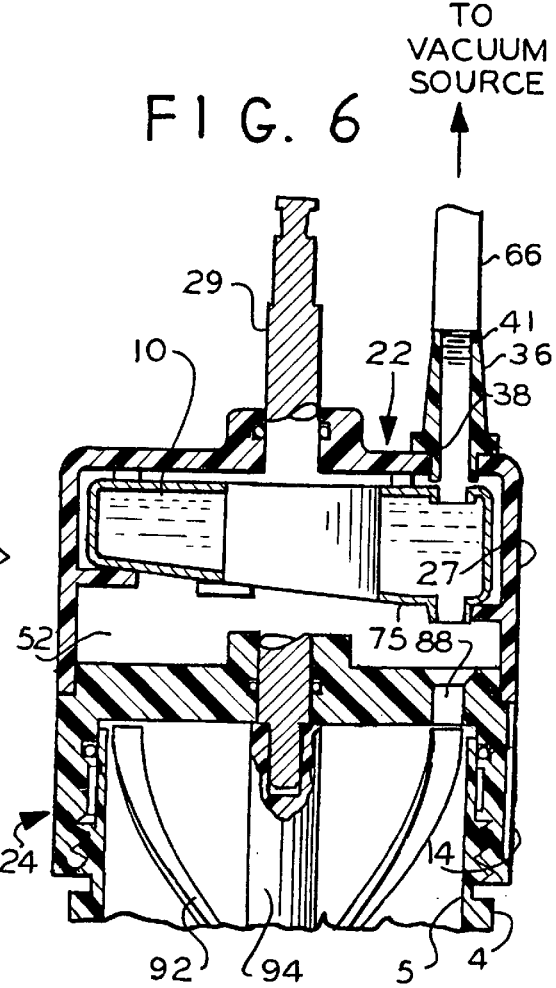
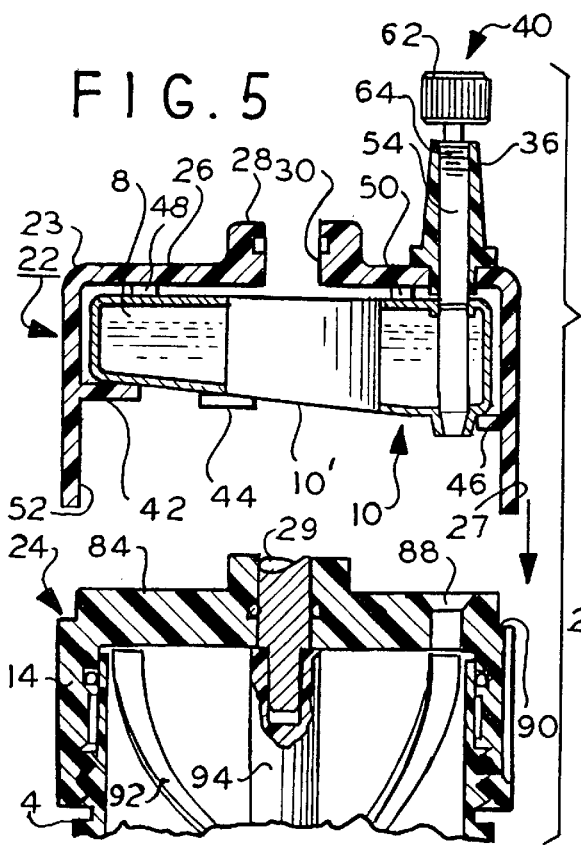

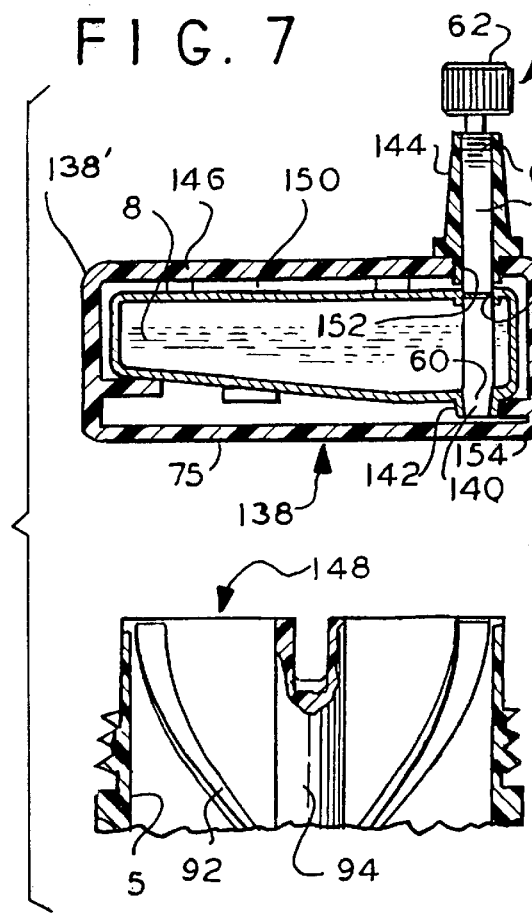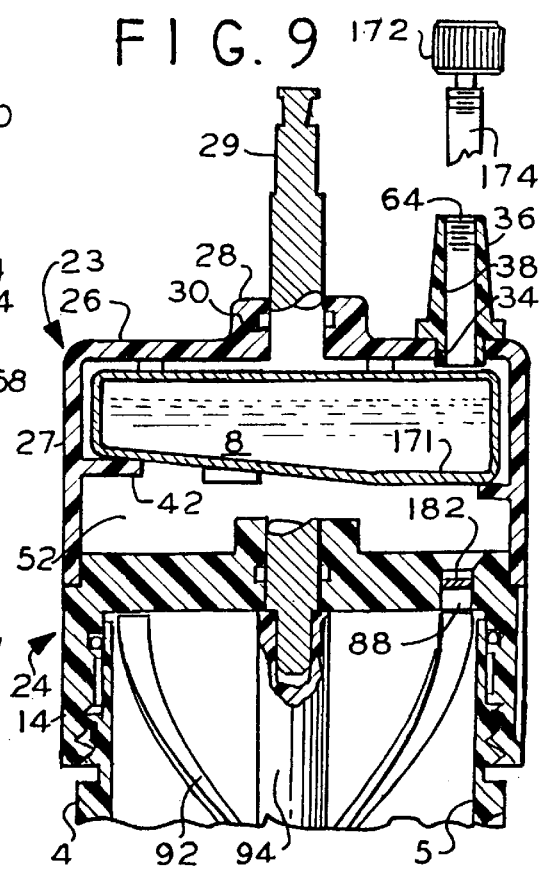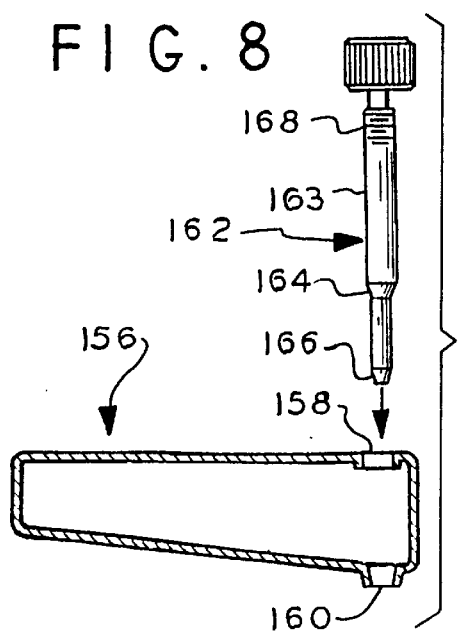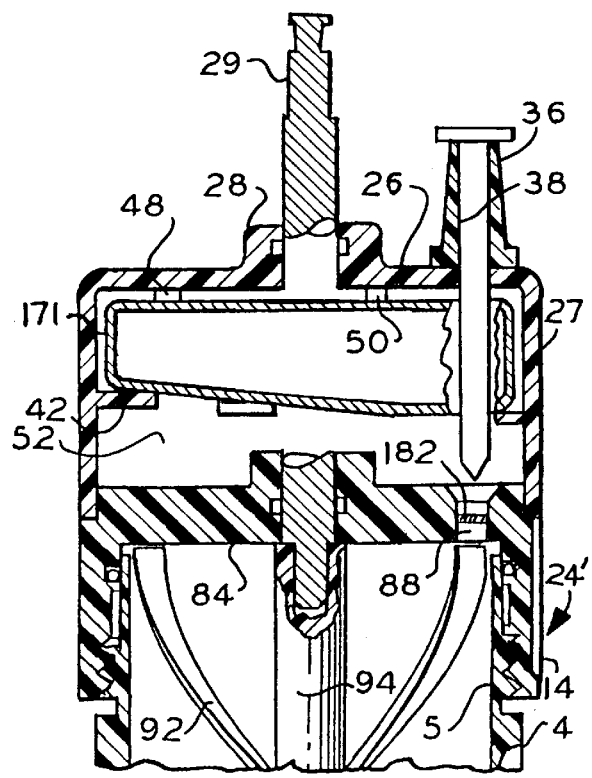

VIAL PACKAGE FOR A BONE CEMENT MIXER AND DISPENSER

This invention relates to frangible glass vial devices for supplying an aggressive liquid monomer such as methyl methacrylate for mixing as part of a two part bone cement including a polymer powder for surgical applications in securing prosthetic devices to bones and joints.

Of interest are copending applications Ser. No. 08/752,003 entitled "Integrated Bone Cement Mixing and Dispensing System" filed Nov. 15, 1996 in the name of Donald Barker et al. now U.S. Pat. No. 5,876,116 (the assignee of the present invention having rights in this application) and commonly owned application Ser. No. 09/010,083 filed Jan. 21,1998 in the name of Bogert et al. entitled "Bone Cement Mixer and Dispenser."

A cement mixing and dispensing device is disclosed in the aforementioned applications. In one device, the components are mixed, entrained air removed, and the mixed cement dispensed without separate handling. After use, the device is discarded. This device works well, however, it requires the manual insertion of the powder component and the liquid component into the device. To do so, the device has a cover over a mixing chamber. The cover is removed and the liquid and powder are then poured into the mixing chamber.

The problem is that, like all prior art systems employing such liquids and cements, the liquid is aggressive and attacks most containers. As a result, the liquid is packaged and sealed in relatively inert glass vials. These vials are frangible. They have a narrowed tapered head connected to a wider body via a reduced diameter neck.

To empty the vial, a nurse in an operating room needs to break open the vial typically by fracturing the head or neck. This is undesirable, as the vial may shatter or, at best, glass fragments can be a problem and must be accounted for and precluded from causing injury. Also, the fractured vial or fragments have sharp edges which undesirably may cut the user or the user's gloves. The vial thus needs to be handled with care and accidents may occur.

In addition, the liquid in the vial has noxious fumes. When the vial is fractured, the fumes escape to the ambient and over long periods of repetitive exposure can be the source of health problems. At best, the fumes are highly unpleasant. In the aforementioned copending applications, the fumes are exhausted by a vacuum connected to the mixing device mixing chamber. However, the fumes still escape in a sufficiently large volume to the ambient as the liquid is poured into the mixing device from the fractured vial as disclosed in the application Ser. No. 08/752,003.

The aforementioned copending application Ser. No. 09/010,083 filed Jan. 21, 1998 (Attorney docket 329578-16) addresses this latter problem by providing a device for receiving at least the head portion of the vial and for fracturing the vial at the head end while constraining the glass fragments after fracturing. The fractured fragments are retained in a housing chamber after the vial head is broken. The vial receiving housing may form a cap for the mixing and dispensing device assembly. However, the intact vial body with a fragmented end needs to be removed and handled separately. This additional handling of the vial is believed not desirable.

A need is seen by the present inventors for a vial packaging assembly for use with a mixing device for such cement which addresses the problem of the additional handling of the vial before and after fracturing. The present inventors recognize a need for providing a cement mixing apparatus wherein the aggressive liquid monomer and vial are self contained as a complete package.

A vial package assembly according to the present invention for a liquid containing vial comprises a housing having a chamber; a vial having a sealed chamber containing the liquid and disposed in the cavity; and means for opening the vial chamber to release the liquid while the vial is in the housing chamber.

In one aspect, the means for opening the vial comprises valve means secured to the vial and housing.

The valve means may comprise a valve stem threaded to the housing, the vial having first and second ports, the stem including male port engaging means for selectively opening and closing the first and second ports.

The means for opening the vial may also comprise means for fracturing the vial into fragments and for retaining the fragments in the housing chamber.

The means for fracturing may comprise means passing through the housing for manually stressing the vial.

The assembly in a further aspect may include means for securing the housing to a bone cement mixing apparatus having a mixing chamber with at least one port for receiving cement powder and liquid components such that the liquid flows from the vial into the mixing chamber through the at least one port.

A bone cement mixing apparatus for mixing a bone cement powder with a monomer liquid contained in a closed vial, the apparatus including a housing having a cement mixing chamber, at least one powder and liquid receiving port and a mixed cement dispensing port, means coupled to the chamber for mixing the powder and liquid and for dispensing the mixed cement through the dispensing port, the combination therewith according to a further aspect of the present invention comprises a cap assembly secured to the housing for enclosing the at least one port and for enclosing the vial containing the liquid and vial opening means for selectively opening the enclosed vial and causing the liquid to flow to the mixing chamber.

In a further aspect, valve means are coupled to the cap assembly for selectively opening and closing the enclosed vial.

In a further aspect, the cap assembly includes a housing having a vial receiving chamber, the valve means including valve operating means coupled to the vial chamber and to the vial and extending externally the cap assembly housing for the selectively opening and closing.

In a further aspect, the cap assembly includes an upstanding nozzle, the nozzle including internal threads for operatively and releaseably coupling the valve operating means thereto and for selectively coupling a vacuum source thereto.

IN THE DRAWING

FIG. 4 is an exploded partially in section elevation view showing the vial liquid filling and assembling process for assembling the vial assembly of FIG. 1;

FIG. 5 is an exploded sectional elevation view showing the assembly of the vial assembly of FIG. 4 to a bone cement mixing and dispensing apparatus;

FIG. 6 is a fragmented sectional elevation view similar to that of FIG. 1 showing the vial valve open, the liquid discharged into the mixing apparatus mixing chamber and a vacuum source coupled to the mixing chamber to evacuate the liquid noxious fumes;

FIG. 7 is an exploded elevation fragmented sectional view of a vial assembly and a mixing and dispensing apparatus for dispensing the liquid component into the dispensing apparatus according to a second embodiment of the present invention;

FIG. 8 is an exploded elevation view partially in section showing a vial and valve assembly according to a third embodiment of the present invention;

FIG. 9 is a fragmented side elevation sectional view of a third embodiment of the present invention showing a frangible vial and cement mixing apparatus for use with a vial fracturing device of FIG. 10;

FIG. 9a is a fragmented side elevation sectional view of the embodiment of FIG. 9 showing the vial fractured by the vial fracturing device of FIG. 10; and FIG. 10 is a side elevation view of an embodiment of a vial fracturing device for fracturing the vials of FIGS. 9 and 9a.

Figure 1:
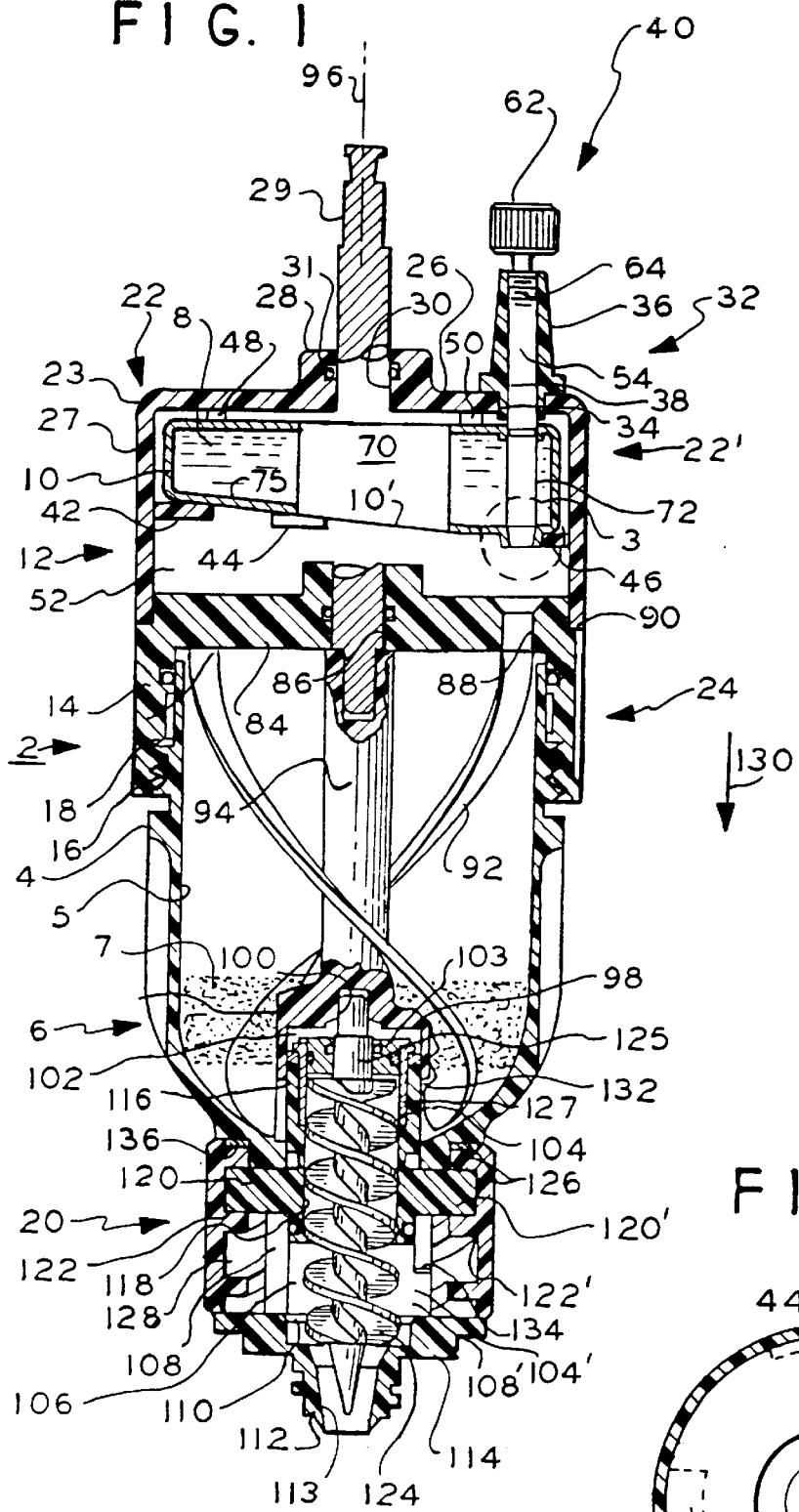
FIG. 1 is a side elevation sectional view of a bone cement mixing and dispensing apparatus according to an embodiment of the present invention prior to mixing of the liquid and powder cement components.
Figure 2:
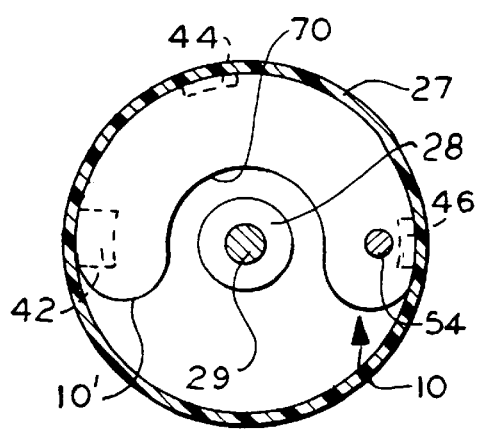
FIG. 2 is a top plan sectional view of the apparatus of FIG. 1.

In FIGS. 1 and 2, apparatus 2 comprises a preferably molded thermoplastic housing 4. The housing 4 has a bone cement mixing chamber 5 containing component mixing assembly 6. The assembly 6 mixes a prepackaged portion of bone cement powder 7 in chamber 5 with a bone cement liquid 8 supplied from a sealed vial 10 which may be glass or other liquid monomer inert material. The apparatus 2 further includes a cover cap assembly 12. The cap assembly 12 comprises a molded thermoplastic lower cover member 24 with a depending outer annular cylindrical skirt 14 and an upper cover subassembly 22 attached to the member 24. The skirt 14 has internal threads 16 which mate with external threads 18 on the housing 4. The apparatus 2 dispenses mixed cement via dispensing assembly 20 at the bottom of the housing 4.

The subassembly 22, FIGS. 1, 4 and 5, comprises an upper cover member 23, preferably molded thermoplastic, a monomer liquid 8 filled vial 10 and a valve assembly 32. The cover member 23 comprises a circular disk 26 with a central boss 28 and a peripheral circular cylindrical skirt 27. The skirt 27 depends from the disk 26 outer peripheral edge. The boss 28 has a bore 30 with an O-ring 31 which slidably and rotatably sealingly receives cylindrical drive shaft 29. Shaft 29 has an upper keyed end that is rotatably driven by a drive source (not shown). The disk 26 has an aperture 34 for receiving the valve assembly 32.

Valve assembly 32 comprises a thermoplastic molded nozzle 36 having a bore 38 for receiving male valve member 40. The bore 38 is coextensive with aperture 34 and has internal threads 41. The nozzle 36 is preferably bonded to the disk 26, but may be secured by other fastening arrangements such as threads, press interference fit or by molding integral one piece with the upper cover member 23.

The male valve member 40 of valve assembly 32, as best seen in FIG. 4, comprises a circular cylindrical glass valve stem 54 having an annular groove 56 in which is seated an O-ring 58. The stem 54 terminates at one end in a preferably ground conical segment valve surface 60. A knob 62 is secured to the stem 54 at the other end and may be formed integral one piece with the stem. External threads 64 are formed in the stem 54 adjacent to the knob 62. Threads 64 mate with and engage the internal threads 41 of the nozzle 36. The exterior surface of the nozzle 36 tapers somewhat to a smaller diameter at the threads 41 for receiving a vacuum source tube 66, FIG. 6. The tube 66 is attached after the valve member 40 is removed as will be explained below.

Molded to the cover member 23 are a plurality of radially inwardly extending vial supporting and retaining flexible projections 42, 44, 46, 48 and 50. The disk 26 and skirt 14 form a chamber 52 in which the vial 10 and projections 42–50 are located.

The vial 10, FIG. 2, has a somewhat kidney, crescent or U-shaped body 10'. The body 10' is held in place in the chamber 52 by the projections 42–50, which preferably snap fit receive the liquid filled body 10', FIG. 4. In the alternative, the projections may be heat deformed after the vial 10 is in position to lock the vial in place. The vial 10 may also be bonded in place in the alternative.

The body 10' has a central trough 70 for receiving the cover member 23 boss 28 to allow the shaft 29 to pass through the chamber 52. The body 10' may also be other shapes, e.g., washer-like, according to a given implementation for fitting within the chamber 52. The vial 10 is preferably formed with a somewhat tapered transverse body 10'. The body 10' wall 75 is inclined relative to the opposite side wall of the vial 10 forming the taper to permit the liquid 8 to flow from the horizontal vial 10 when the valve of assembly 32 is opened.

Figure 3:
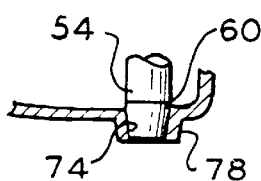
FIG. 3 is a more detailed sectional view of a vial liquid discharge valve taken at region 3 in FIG. 1.

The body 10' wider end 72, FIG. 4, has two aligned valve ports 74 and 76 in corresponding opposing side walls. Each port is formed with a preferably ground valve seat. As best seen in FIG. 3, the seat 74 is conical to axially mate with the stem 54 conical male valve surface 60. The seat 74 is formed in a projection 78 extending from the vial body 10'. The seat 76 is circular cylindrical and may be formed in a projection 76' to sealingly, slidably receive the O-ring 58 on the valve stem 54 (FIG. 4) forming a male valve member.

When the valve stem surface 60 is engaged with seat 74, the O-ring 58 is simultaneously engaged with seat 76. These two simultaneous valve engagements seal the liquid 8 in the vial chamber. The valve stem 54 valve members are rotated into and out of sealing mating position with the respective mating valve seats via the threads 41 and 64.

The subassembly 22 is assembled as shown In FIG. 4. To fill the vial 10, the body 10' is oriented vertically as shown with the valve ports 74 and 76 uppermost. The vial 10 is filled with the liquid cement monomer from a source 80. The liquid is filled via either of the ports 74 and 76.

After the vial 10 is filled with the liquid 8, the filled vial 10 is secured to the cover member 23 chamber 52, direction 82. Not shown are apparatus for holding and manipulating the vial 10, member 23 and valve member 40 during assembly. Such apparatus are within the skill of one of ordinary skill in this art. After the vial 10 is filled and assembled to the member 23, the valve member 40 is attached to the nozzle 36. The valve member 40 seals the ports 74 and 76 of the vial 10 sealing the liquid 8 in the vial 10 chamber. This forms the vial 10 and cover member 23 into the subassembly 22, FIG. 5.

The lower cover member 24, FIG. 1, comprises a disk 84 having a central shaft 29 receiving bore 86. An O-ring in the bore 86 engages the shaft 29 passing therethrough in sealing rotatable sliding relation. A port 88 is in the disk 84. The port 88 is vertically axially aligned with the ports 74 and 76 of the vial 10 when the subassembly 22 is attached to the cover member 24.

The circular cylindrical skirt 14 of member 24 depends from the disk 84. The skirt 14 has an annular shoulder 90. The shoulder 90 receives the bottom annular edge of the skirt 27. The skirt 14 edge region at the shoulder 90 is then bonded to the skirt 27 with an adhesive (not shown) or by heat welding forming the cap assembly 12. This permanently secures the subassembly 22 to the cover 24 and encloses the vial 10 in the chamber 52. In normal use of the apparatus 2, the subassembly 22 is vertically over the cover 24 and housing 4 as shown, FIG. 1.

The mixing assembly 6 includes molded thermoplastic helically extending mixing paddles 92 secured to central shaft 94 which rotates about axis 96 in housing 4 chamber 5. The mixing assembly 6 is also described in more detail in the aforementioned copending applications incorporated by reference herein.

The shaft 94 has an upper central axially extending drive bore. The drive shaft 29 has keyed lower and upper drive ends, e.g.; hex shaped. The upper end is driven by a power source (not shown). The shaft 29 lower end mates in a complementary keyed drive bore of shaft 94 for rotating the paddles 92. The shaft 94 has a lower axially extending cylindrical boss 98. In boss 98 is a central downwardly extending keyed bore 100 and a circular cylindrical bore 102 concentric with and in communication with bore 100. The base of the chamber 5 has central axially extending through bore 104 axially aligned with bores 100 and 102.

The housing 4 includes a depending thermoplastic integral one piece molded extension comprising two diametrical opposite spaced apart tips 106 (one being shown). The tips 106 form a support for the dispensing assembly 20 and form two diametrically opposing axially and radially extending slots 108, 108'. The tips 106 form therebetween an axially extending central bore 104' which is coextensive with bore 104 and is in communication with slots 108, 108'. The tips 106 have a bottom edge 110 to which nozzle 112 is attached via nozzle flange 114 by screws (not shown). The nozzle 112 has a bone cement dispensing discharge conduit 113.

A cylindrical washer-like preferably metal member 103 is secured in bore 102 to auger 124. Member 103 has a central bore through which the auger 124 shaft 125 passes into engagement with bore 100. An O-ring is in respective corresponding grooves in member 103 radial inner and outer surfaces. A metal circular cylindrical sleeve 127 is attached to the inner bore of an outer thermoplastic circular cylindrical sleeve 116. Sleeve 127 slidably and rotationally engages the member 103 outer O-ring. Sleeve 127 has an upper radially outwardly extending flange extending over the upper edge of sleeve 116. The sleeves 116 and 127 form an axially depending circular inner cylindrical cement dispensing channel 118 concentric with the axis 96.

Sleeve 116 is located in bore 102 and includes an O-ring captured between the inner sleeve 127 flange and the upper edge of outer sleeve 116. The latter O-ring is in contact with the bore 102 inner side wall. Sleeve 127 may be pressed into the sleeve 116. The auger 124 and member 103 rotate relative to the sleeves 116 and 127 which do not rotate.

Sleeves 116 and 127 are secured for selective axial downward displacement out of bore 102 on axis 96. The sleeve 116 is slidably sealed to the boss 98 bore 102 by its upper O-ring. The sleeve 116 outer peripheral surface is sealed to the bore 104 by a second intermediate O-ring located in a second sleeve 129 groove. The second O-ring is axially spaced beneath the upper end O-ring.

The two sleeve 116 O-rings are axially aligned and respectively seal the channel 118 and bore 104 in fluid isolation to the chamber 5 in the respective upper and lower positions of the sleeve 116. The O-rings confine the cement components to the chamber 5 during mixing in the sleeve 116 upper position shown.

A pair of diametrically opposite radially outwardly extending circular cylindrical rods form ears 120, 120' and extend from the sleeve 116 outer surface. The ears 120 and 120' pass through and axially displace in corresponding respective slots 122, 122'. A third lowermost O-ring is secured to and in a sleeve 116 outer groove. The third O-ring seals the sleeve 116 to the bore 104' at the lowermost sleeve end beneath the ears 120, 120'.

Auger 124 is secured for rotation about the axis 17. The auger 124 is complementary keyed to the bore 100. The other auger end is in the nozzle 112 discharge conduit 113. The auger is rotatably driven about axis 96 by the rotation of the shaft 29. The auger feeds mixed cement selectively supplied to channel 118 from chamber 5 port 132 to the cement discharge conduit 113.

An axially extending outer cylindrical collar 126 concentric with axis 96 and sleeve 116 is rotatably secured between the nozzle 112 flange 114 and a shoulder 136 at the base of the housing 4 beneath the chamber 5. The collar 126 is manually rotated and rotates in abutting relation to housing 4 shoulder 136 and nozzle 112 flange 114. The collar 126 has an internal helix thread 128. The ears 120, 120' mate with and engage the thread 128. When the collar is manually rotated, the helical thread 128 axially displaces the sleeve 116 downward in direction 130.

In the most downward position (not shown) of the sleeve 116, the uppermost O-ring seats against the bore 104, sealing the chamber 5 from the ambient at the sleeve 116 external surface. In this position, the sleeve 116 upper end is approximately flush with the chamber 5 bottom surface forming a cement receiving port 132 between the boss 98 and chamber 5 bottom surface. The port 132 provides fluid communication between chamber 5 and sleeve channel 118.

A depending finger 134 is molded thermoplastic material integral one piece with one of the housing tips 106. The finger 134 is located with its tip region in slot 122' which resiliently abuts ear 120' in a direction transverse direction 130. When the sleeve 116 is in its lowermost position (not shown), the ear 120' displaces beneath the depending end of the finger 134. The finger 134 then snaps into its normal quiescent position above the ear 120' in the slot 122' locking the sleeve 116 in this lowermost position. This prevents raising the sleeve 116 and reuse of the device 2.

The vacuum receiving nozzle 36, FIG. 6, fluid couples the chambers 5 and 52 to the external ambient atmosphere. The nozzle 36 releasably attaches a vacuum device thereto via tube 66 to exhaust noxious fumes from the mixing chamber 5 and chamber 52 during mixing of the cement after the liquid 8 in the vial is released.

In operation, the cement mixing apparatus 2 is supplied a user as illustrated in FIG. 1. The drive shaft 29 is permanently attached to the apparatus and seals the chambers 5 and 52 via O-rings in the mating bores 30 and 86. The cement component powder 7 and liquid filled vial 10 are prepackaged in the apparatus 2 as described above. The valve member 40 is then detached from the bore 38 in the nozzle 36 with the vial 10 horizontal as shown. This opens the vial ports 74 and 76. The vial 10 bottom wall 75 is inclined relative to the horizontal with the axis 96 vertical. Gravity flows the liquid 8 to the vial discharge port 74. The liquid 8 then flows through the port 88 in the lower cover member 24 disk 84 into the chamber 5. The vacuum is then applied to the chambers 52 and 5 by connecting vacuum source tube 66 to nozzle 36, FIG. 6. to evacuate the noxious fumes.

The paddles 92 are then rotated and the powder and liquid 8 mixed to form the cement. When thoroughly mixed, the collar 126 is rotated to lower the sleeve 116 and open the chamber 5 discharge port 132 to channel 118. Power is applied to the auger 124 via shaft 94. The auger 124 feeds the mixed cement to the discharge conduit 113 in the nozzle 112. With the sleeve 116 locked in the lowermost position (not shown) by the finger 134, the apparatus 2 can not be reused and is discarded with the empty vial 10 entrapped therein.

In a second embodiment in FIG. 7, liquid filled glass vial 150 is packaged in a self contained molded thermoplastic container 138. The vial may be filled as shown in FIG. 4. The vial has ports 152 and 154 which are identical to ports 74 and 76 described above. The container 138 encloses the liquid filled vial 150 and forms a separate package. The vial 150 may be a circular pancake style unit or may have any desired configuration. The container is preferably formed in multiple pieces (not shown) that are later attached by heat welding, adhesive bonding or by snap fit attachment. The container 138 has a discharge port 140 formed by discharge nozzle 142.

A nozzle 144 is attached to a side 146 of the container opposite the nozzle 142. The nozzle 144 has an internal thread for mating with the valve member 40 threads. The nozzles 142 and 144 are preferably molded one piece with the container 138 body 138'. The nozzles 142 and 144 are axially aligned with the vial 150 ports 152 and 154. In the alternative, the nozzle 144 may be omitted and its internal threads may be formed in the side 146 of the container 138 or in a small boss (not shown) on that side of the container.

The valve member 40 is inserted in and threaded to the nozzle 144 to seal the vial ports 152 and 154 in a method similar to that shown in FIG. 4. The mixing assembly 148 has a prior art cover (not shown). This cover may be removed to pour the powder (not shown) and liquid into the housing 4 chamber 5. In the alternative, the powder may be prepackaged in the assembly 148 chamber.

In use, the nozzle 144 is placed vertically above the mixing chamber 5. The valve member 40 is removed to discharge the liquid 8 into the mixing chamber. The cover is then replaced over the housing 4 and the fumes evacuated via a nozzle (not shown) attached to that cover.

FIG. 8 illustrates a further embodiment of a vial and valve assembly. Vial 156 which may be glass is formed with two ports 158 and 160. Each port is ground with a conical segment valve seat. The vial otherwise may be identical to the vial 10, FIG. 1. Valve member 162 has a stem 163 including a male valve conical segment 164 which mates with the valve seat at port 158 and a male valve conical segment 166 which mates with the valve seat at port 160. The stem 163 has threads 168 which mate with the threads in the cover subassembly nozzle, such as nozzle 36, FIG. 1.

FIGS. 9 and 9a illustrate a further embodiment. Cover subassembly 170 includes upper cover member 23 and lower cover member 24 as described above in connection with FIG. 1. The difference is that a frangible glass monomer liquid filled vial 171 is provided which is sealed without the ports as in vial 10, FIG. 1. The vial 170 except for the omitted ports is otherwise identical to vial 10.

A knob 172 with a threaded stem 174 is inserted and threaded into nozzle 36 bore 38. The knob and stem may be of any suitable material such as plastic or metal and so on. A metal pin 176, FIG. 10, is used to open the vial. The pin 176 has a head 178 and a shank 180 with a pointed tip.

In FIG. 9a, the pin 176 is inserted in the nozzle 36 bore 38 until it engages the vial. The pin 176 is then forced against the vial stressing and fracturing the vial. The head 178 abuts the nozzle 36 to limit insertion of the pin 176 to completely fracture the vial. This permits the liquid to flow into the mixing chamber 5 of housing 4.

A fine mesh glass fragment particle filter 182 is secured in port 88 of the lower cover 24', which is otherwise identical to cover 24, FIG. 1. The filter 182 has a micromesh pore size sufficiently large to pass therethrough the monomer liquid mixing component from the vial 171 while capturing and filtering out glass fragments from the liquid. The filter 182 may comprise any known particulate filtering substrate inert to the liquid 8. The glass fragments are retained by the filter 182 in the vial receiving chamber 52.

The filter 182 may be secured in place by heat deformation of the disk 84. In the alternative, the filter may be bonded by a suitable adhesive or other arrangement. The filter 182 may also be secured by ribs (not shown) in or adjacent to the port 88. The disk 84 surface in the chamber 5 is preferably flush. In the alternative, other means may be provided for fracturing the vial such as levers and the like.

There thus has been shown a bone cement and mixing apparatus having a mixing chamber with prepackaged bone cement powder and liquid components. The apparatus mixes the bone cement powder and liquid components. A bone cement liquid filled vial is enclosed in an apparatus chamber or may be supplied in a separate package. The chamber may be formed integral with the mixing apparatus in a cover subassembly. The vial is opened by a valve member attached to a cap assembly attached to the mixing apparatus or to the separate package. In the alternative, the vial when formed of frangible glass may be opened by fracturing it while it is enclosed in the chamber confining the glass fragments. The vial chamber has a filter that traps glass fragments in the chamber when the vial is fractured.

Different devices are shown which may be used to enclose the vial and for selectively opening the vial to release its liquid contents.

It will occur to one of ordinary skill that various modifications may be made to the disclosed embodiments. It is intended that the disclosed embodiments are given by way of illustration and not limitation. The invention is defined by the appended claims.

What is claimed is:

1. A vial package assembly for a liquid containing glass vial comprising:

a housing having a chamber;

a vial having a sealed chamber containing said liquid and disposed in the housing chamber; and valve means secured to the vial and housing for opening the vial chamber to release the liquid while the vial is in said housing chamber.

2. The assembly of claim 1 wherein the valve means comprises a valve stem threaded to the housing, said vial having first and second ports, said stem including male port engaging means for selectively opening and closing said first and second ports.

3. The assembly of claim 1 wherein the liquid is a bone cement monomer and including means for securing the housing to a bone cement mixing apparatus having a mixing chamber for mixing bone cement powder and liquid components such that the liquid monomer flows from the vial into said mixing chamber.

4. A vial package assembly comprising:

a vial having a chamber containing said liquid, said vial having at least one port in fluid communication with the chamber;

valve means normally engaged with the at least one port and including valve operating means for selectively opening the at least one port; and a vial housing for substantially enclosing the vial, said valve operating means extending externally the housing for said selective opening of the at least one port.

5. The assembly of claim 4 wherein the at least one port comprises a female tapered seat, said valve comprising a tapered male valve member for mating with and fluid sealing engagement with said seat.

6. The assembly of claim 4 wherein said vial has first and second axially aligned ports each forming a valve seat, said valve means including a male valve member having first and second valve elements each for respectively simultaneously engaging in fluid sealing contact a corresponding different one of said valve seats.

7. The assembly of claim 6 wherein the housing has a threaded port, the male member including a valve stem forming said elements, said stem including threads for engagement with said housing threaded port.

8. The assembly of claim 4 wherein the housing has first and second ports, the vial having third and fourth ports, the third port being adjacent to and fluid coupled to the first port and the fourth port being adjacent to and fluid coupled to the second port, the valve means for selectively opening and closing the third and fourth ports.

9. The assembly of claim 8 wherein the valve means comprises a valve seat at each said third and fourth ports and the valve operating means comprises a stem with first and second male seat engaging elements for engaging a different corresponding valve seat on said vial, said stem for protruding through the first port.

10. The assembly of claim 9 wherein the stem is threaded to the housing at the first port.

11. The assembly of claim 4 including means for securing the housing to a bone cement mixing apparatus having a mixing chamber such that the liquid flows from the vial into said mixing chamber from the opened at least one port.

12. The assembly of claim 11 wherein the mixing apparatus includes a mixing housing forming a mixing chamber having at least one cement liquid inlet, said means for securing comprising a skirt for engaging the mixing housing adjacent to said at least one inlet, said vial housing for enclosing said at least one inlet.

13. A bone cement mixing apparatus for mixing a bone cement powder with a monomer liquid contained in a closed vial, said apparatus including a housing having a cement mixing chamber, at least one liquid receiving port and a mixed cement dispensing port, means coupled to the chamber for mixing bone cement powder and liquid in the chamber and for dispensing the mixed cement through said dispensing port, the combination therewith comprising:

a cap assembly secured to the housing for enclosing said at least one port and for enclosing said vial containing said liquid; and vial opening means comprising valve means coupled to the cap assembly for selectively opening and closing said enclosed vial and for causing said liquid to flow to said mixing chamber.

14. The apparatus of claim 13 wherein said cap assembly includes a housing having a vial chamber, said vial being received in the vial chamber, said valve means including valve operating means coupled to the vial chamber and to the vial and extending externally the cap assembly housing for said selectively opening and closing.

15. The apparatus of claim 14 wherein the cap assembly includes an upstanding nozzle, said nozzle including internal threads for operatively and releaseably coupling said valve operating means thereto and for selectively coupling a vacuum source thereto.

16. The apparatus of claim 13 wherein the housing has first and second ports, the vial having third and fourth ports, the third port being adjacent to and fluid coupled to the first port and the fourth port being adjacent to and fluid coupled to the second port, the valve means for selectively opening and closing the third and fourth ports.

17. A bone cement mixing device comprising:

a housing forming a bone cement mixing chamber;

a mixing device coupled to the housing for mixing liquid and powder bone cement components in the mixing chamber;

a cover comprising an intermediate cap enclosing the mixing chamber and a cover cap over the intermediate cap forming a second chamber, the cover being releasably secured to the housing for providing a cement powder component receiving port, said cover second chamber for receiving at least a portion of the vial and the liquid component from the vial, an opening in the cover for providing fluid communication between said second chamber and said mixing chamber; and opening means for opening the vial portion received in said second chamber.

18. The device of claim 17 wherein the opening means comprises means for fracturing the vial portion in said second chamber.

19. The device of claim 17 wherein the opening means comprises valve means coupled to the cover and to the vial received vial portion for selectively opening and closing the received vial portion.

\* \* \* \* \*